(12) United States Patent
Smith (10) Patent No.: US 8,653,994 B2
(45) Date of Patent: Feb. 18, 2014

(54) SYSTEM AND METHOD FOR DETECTION OF ADC ERRORS

(75) Inventor: Robert B. Smith, Loveland, CO (US)

(73) Assignee: Covidien LP, Mansfield, MA (US)

( * ) Notice: Subject to any disclaimer, the term of this patent is extended or adjusted under 35 U.S.C. 154(b) by 17 days.

(21) Appl. No.: 13/426,204

(22) Filed: Mar. 21, 2012

(65) Prior Publication Data
US 2013/0249721 A1   Sep. 26, 2013

(51) Int. Cl.
*H03M 1/10* (2006.01)

(52) U.S. Cl.
USPC .......................................... 341/120; 341/155

(58) Field of Classification Search
USPC ............ 341/120, 118, 155, 119; 324/67, 533, 324/534, 307.2, 300, 322, 318, 314
See application file for complete search history.

(56) References Cited

U.S. PATENT DOCUMENTS

| | | | |
|---|---|---|---|
| 4,378,801 A | 4/1983 | Oosten | |
| 4,524,444 A * | 6/1985 | Efron et al. | 714/735 |
| 4,569,345 A | 2/1986 | Manes | |
| 4,739,759 A | 4/1988 | Rexroth et al. | |
| 4,788,634 A | 11/1988 | Schlecht et al. | |
| 5,161,893 A | 11/1992 | Shigezawa et al. | |
| 5,300,068 A | 4/1994 | Rosar et al. | |
| 5,318,563 A | 6/1994 | Malis et al. | |
| 5,452,725 A | 9/1995 | Martenson | |
| 5,531,774 A | 7/1996 | Schulman et al. | |
| 5,556,396 A | 9/1996 | Cohen et al. | |
| 6,144,937 A * | 11/2000 | Ali | 704/233 |
| 6,287,304 B1 | 9/2001 | Eggers et al. | |
| 6,370,408 B1 | 4/2002 | Merchant et al. | |
| 6,391,024 B1 | 5/2002 | Sun et al. | |
| 6,458,121 B1 | 10/2002 | Rosenstock et al. | |
| 6,672,151 B1 | 1/2004 | Schultz et al. | |
| 6,819,027 B2 | 11/2004 | Saraf | |
| 7,041,096 B2 | 5/2006 | Malis et al. | |
| 7,184,820 B2 | 2/2007 | Jersey-Willuhn et al. | |
| D574,323 S | 8/2008 | Waaler | |
| 7,422,582 B2 | 9/2008 | Malackowski et al. | |
| 2007/0093801 A1 | 4/2007 | Behnke | |
| 2008/0234574 A1 | 9/2008 | Hancock et al. | |
| 2010/0063494 A1 | 3/2010 | Orszulak | |
| 2010/0063497 A1 | 3/2010 | Orszulak | |
| 2010/0168730 A1 | 7/2010 | Hancock et al. | |

FOREIGN PATENT DOCUMENTS

| | | |
|---|---|---|
| DE | 179607 | 3/1905 |
| DE | 1099658 | 2/1961 |
| DE | 1139927 | 11/1962 |
| DE | 1149832 | 6/1963 |

(Continued)

OTHER PUBLICATIONS

U.S. Appl. No. 10/406,690, filed Apr. 3, 2003, Robert J. Behnke, II.

(Continued)

*Primary Examiner* — Joseph Lauture (57) ABSTRACT

The present disclosure provides for a system for testing an analog-to-digital converter. The system includes a test pulse source configured to provide a test pulse signal; a test circuit coupled to the test pulse source and configured to provide an analog decaying voltage signal in response to the test pulse signal; and an analog-to-digital converter coupled to the test circuit and configured to convert the analog decaying voltage signal into a digital decaying voltage signal.

16 Claims, 5 Drawing Sheets

(56) References Cited

FOREIGN PATENT DOCUMENTS

| | | |
|---|---|---|
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| DE | 10 2008058737 | 4/2010 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 882955 | 12/1998 |
| EP | 1051948 | 11/2000 |
| EP | 1366724 | 1/2006 |
| EP | 880220 | 6/2006 |
| EP | 1776929 | 4/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| JP | 63 005876 | 1/1988 |
| SU | 166452 | 1/1965 |
| SU | 727201 | 4/1980 |
| WO | WO95/19148 | 7/1995 |
| WO | WO96/08794 | 3/1996 |
| WO | WO02/11634 | 2/2002 |
| WO | WO02/45589 | 6/2002 |
| WO | WO03/090635 | 11/2003 |
| WO | WO2005/115235 A1 | 12/2005 |
| WO | WO2006/050888 | 5/2006 |
| WO | WO2008/043999 A2 | 4/2008 |
| WO | WO2008/053532 | 5/2008 |
| WO | WO2008/110756 A2 | 9/2008 |

OTHER PUBLICATIONS

U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 12/985,063, filed Jan. 5, 2011, Robert J. Behnke, II.
U.S. Appl. No. 13/034,822, filed Feb. 25, 2011, Mark A. Johnston.
U.S. Appl. No. 13/048,639, filed Mar. 15, 2011, James S. Cunningham.
U.S. Appl. No. 13/049,459, filed Mar. 16, 2011, James H. Orszulak.
U.S. Appl. No. 13/050,770, filed Mar. 17, 2011, Robert B. Smith.
U.S. Appl. No. 13/085,258, filed Apr. 12, 2011, Ronald J. Podhajsky.
U.S. Appl. No. 13/085,278, filed Apr. 12, 2011, James A. Gilbert.
U.S. Appl. No. 13/118,973, filed May 31, 2011, James H. Orszulak.
U.S. Appl. No. 13/186,092, filed Jul. 19, 2011, George J. Collins.
U.S. Appl. No. 13/186,107, filed Jul. 19, 2011, George J. Collins.
U.S. Appl. No. 13/186,121, filed Jul. 19, 2011, George J. Collins.
U.S. Appl. No. 13/195,607, filed Aug. 1, 2011, James H. Orszulak.
U.S. Appl. No. 13/221,424, filed Aug. 30, 2011, James E. Krapohl.
U.S. Appl. No. 13/228,996, filed Sep. 9, 2011, Robert B. Smith.
U.S. Appl. No. 13/236,997, filed Sep. 20, 2011, Robert J. Behnke, II.
U.S. Appl. No. 13/237,068, filed Sep. 20, 2011, Robert J. Behnke, II.
U.S. Appl. No. 13/237,187, filed Sep. 20, 2011, Robert J. Behnke, II.
U.S. Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/247,043, filed Sep. 28, 2011, Donald W. Heckel.
U.S. Appl. No. 13/358,129, filed Jan. 25, 2012, Joseph D. Brannan.
U.S. Appl. No. 13/360,140, filed Jan. 27, 2012, James E. Krapohl.
U.S. Appl. No. 13/362,548, filed Jan. 31, 2012, Steven P. Buysse.
U.S. Appl. No. 13/362,816, filed Jan. 31, 2012, Steven P. Buysse.
U.S. Appl. No. 13/424,127, filed Mar. 19, 2012, Robert J. Behnke, II.
U.S. Appl. No. 13/426,204, filed Mar. 21, 2012, Robert B. Smith.
U.S. Appl. No. 13/442,460, filed Apr. 9, 2012, James E. Krapohl.
U.S. Appl. No. 13/446,096, filed Apr. 13, 2012, James H. Orszulak.
U.S. Appl. No. 13/469,960, filed May 11, 2012, Robert J. Behnke, II.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" in William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.

(56) References Cited

OTHER PUBLICATIONS

Zlatanovic M., "Sensors in Diffusion Plasma Processing" Microelectronics 1995; Proceedings 1995; 20$^{th}$ International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP09763515.5 dated Nov. 29, 2011.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179305.7 dated Aug. 23, 2011.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11006233.8 dated Feb. 2, 2012.
International Search Report EP11155959.7 dated Jun. 30, 2011.
International Search Report EP11155960.5 dated Jun. 10, 2011.
International Search Report EP11168660 dated Sep. 28, 2011.
International Search Report EP11170959.8 dated Dec. 9, 2011.
International Search Report EP11173562.7 dated Nov. 24, 2011.
International Search Report EP11182150.0 dated Nov. 17, 2011.
International Search Report EP11188798.0 dated Dec. 27, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.

* cited by examiner

SYSTEM AND METHOD FOR DETECTION OF ADC ERRORS

BACKGROUND

1. Technical Field

The present disclosure relates to an electrosurgical system and method for operating an electrosurgical generator. More particularly, the present disclosure relates to a system and method for detecting and mitigating errors associated with analog-to-digital converters (ADC).

2. Background of Related Art

Electrosurgery involves application of high radio frequency electrical current to a surgical site to cut, ablate, or coagulate tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact of body tissue with either of the separated electrodes prevents current flow.

Bipolar electrosurgery generally involves the use of forceps. A forceps is a pliers-like instrument, which relies on mechanical action between its jaws to grasp, clamp and constrict vessels or tissue. So-called "open forceps" are commonly used in open surgical procedures whereas "endoscopic forceps" or "laparoscopic forceps" are, as the name implies, used for less invasive endoscopic surgical procedures. Electrosurgical forceps (open or endoscopic) utilize mechanical clamping action and electrical energy to effect hemostasis on the clamped tissue. The forceps include electrosurgical conductive surfaces, which apply the electrosurgical energy to the clamped tissue. By controlling the intensity, frequency and duration of the electrosurgical energy applied through the conductive plates to the tissue, the surgeon can coagulate, cauterize and/or seal tissue.

Tissue or vessel sealing is a process of liquefying the collagen, elastin and other compounds in the tissue so that they reform into a fused mass with significantly reduced demarcation between the opposing tissue structures. Cauterization involves the use of heat to destroy tissue and coagulation is a process of desiccating tissue wherein the tissue cells are ruptured and dried.

Tissue sealing procedures involve more than simply cauterizing or coagulating tissue to create an effective seal; the procedures involve precise control of a variety of factors. For example, in order to affect a proper seal in vessels or tissue, it has been determined that two predominant mechanical parameters must be accurately controlled: the pressure applied to the tissue; and the gap distance between the electrodes (i.e., distance between opposing jaw members or opposing sealing surfaces). In addition, electrosurgical energy must be applied to the tissue under controlled conditions to ensure creation of an effective vessel seal.

Electrosurgical procedures outlined above may utilize various tissue and energy parameters in a feedback-based control system. There is continual need to improve sensors as well as systems and method for processing the sense signals.

SUMMARY

According to one aspect of the present disclosure, a system for testing an analog-to-digital converter is disclosed. The system includes a test pulse source configured to provide a test pulse signal; a test circuit coupled to the test pulse source and configured to provide an analog decaying voltage signal in response to the test pulse signal; and an analog-to-digital converter coupled to the test circuit and configured to convert the analog decaying voltage signal into a digital decaying voltage signal.

In other aspects of the present disclosure, the system may also include a controller coupled to the analog-to-digital converter.

In further aspects of the present disclosure, the controller may include a memory storing a predetermined digital decaying voltage response of the analog-to-digital converter.

In additional aspects of the present disclosure, the controller is configured to compare the digital decaying voltage signal to the predetermined digital decaying voltage response.

According to another aspect of the present disclosure, an electrosurgical system is disclosed. The system includes a radio frequency output stage configured to generate radio frequency energy; a sensor coupled to the radio frequency output stage configured to sense at least one property of the radio frequency energy; and a test pulse source configured to provide a test pulse signal. The system further includes a test circuit coupled to the test pulse source and configured to provide an analog decaying voltage signal in response to the test pulse signal; an analog-to-digital converter coupled to the test circuit and configured to convert the analog decaying voltage signal into a digital decaying voltage signal; and a controller coupled to the analog-to-digital converter, the controller including a memory storing a predetermined digital decaying voltage response of the analog-to-digital converter, wherein the controller is configured to compare the digital decaying voltage signal to the predetermined digital decaying voltage response.

The system according to any of the above-described aspects of the present disclosure may include a test pulse source configured to provide a tri-state digital output.

In additional aspects, the controller may be further configured to output an error signal in response to a deviation between the digital decaying voltage signal and the predetermined digital decaying voltage response.

According to a further aspect of the present disclosure, a method for testing an analog-to-digital converter is provided. The method includes: providing a test pulse signal to a test circuit coupled to the analog-to-digital converter; generating an analog decaying voltage signal in response to the test pulse signal; and converting the analog decaying voltage signal into a digital decaying voltage signal.

In additional aspects, the method may include storing a predetermined digital decaying voltage response of the analog-to-digital converter in a memory; and comparing the digital decaying voltage signal to the predetermined digital decaying voltage response.

In further aspects, the method may also include outputting an error signal in response to a deviation between the digital decaying voltage signal and the predetermined digital decaying voltage response.

In other aspects, the test circuit of any of the above-described aspects of the present disclosure may include an input coupled to the test pulse source; a resistor coupled to the input; a capacitor coupled to the resistor; and an output coupled to the capacitor and the analog-to-digital converter.

In further aspects, the resistor may be coupled in series with the capacitor.

In additional aspects, the test circuit of any of the above-described aspects of the present disclosure may include a diode coupled to the input and the resistor.

In other aspects, the resistor may be coupled in parallel with the capacitor.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The present disclosure provides an electrosurgical generator and circuit for detecting the failure in analog-to-digital converters (ADC). ADCs are utilized to convert various analog signals (e.g., voltage and current sensor signals) into digital signals for subsequent processing by controllers of the electrosurgical generators. A faulty ADC results in a loss of conversion linearity, scale, monotonicity, and combination thereof. These types of errors may be caused by a faulty reference voltage signal and/or stuck or shorted bit(s).

In ADC applications where detection and mitigation of measurement errors is imperative, e.g., in medical devices and life support systems, it is important to provide redundant and/or independent systems and methods for detecting such errors quickly and reliably. Further, it is desirable for such systems and method to be as simple and reliable as possible to minimize the chances of additional errors and/or false error indications.

The present disclosure provides a system and a method for determining operational state of the ADC. The system and method includes a circuit having a known resistance value (e.g., resistor) and a current integrator (e.g., a capacitor). The voltage response of the circuit may then be analyzed using mathematical formulas that represent the response of the circuit. It is possible to accurately deduce the value of a resistance of the test circuit coupled to the ADC by integrating the current through the resistance with a known impressed voltage and a series-connected capacitor as a current integrator. In embodiments, the resistance may be determined by either measuring the voltage across the capacitor at a fixed time or by measuring the elapsed time for the voltage across the capacitor to reach a fixed value. Either method provides a value that is mathematically related to the value of the resistance under test. Any significant deviation from the measured resistance would be indicative of the fault with the ADC. This configuration represents a very simple, stable and reliable circuit that can be re-arranged various ways.

A generator according to the present disclosure can perform monopolar and/or bipolar electrosurgical procedures, including vessel-sealing procedures. The generator may include a plurality of outputs for interfacing with various electrosurgical instruments (e.g., a monopolar instrument, return electrode, bipolar electrosurgical forceps, footswitch, etc.). Further, the generator includes electronic circuitry configured to generate radio frequency energy specifically suited for various electrosurgical modes (e.g., cutting, blending, division, etc.) and procedures (e.g., monopolar, bipolar, vessel sealing). In embodiments, the generator may be embedded, integrated or otherwise coupled to the electrosurgical instruments providing for an all-in-one electrosurgical apparatus.

Figure 1:
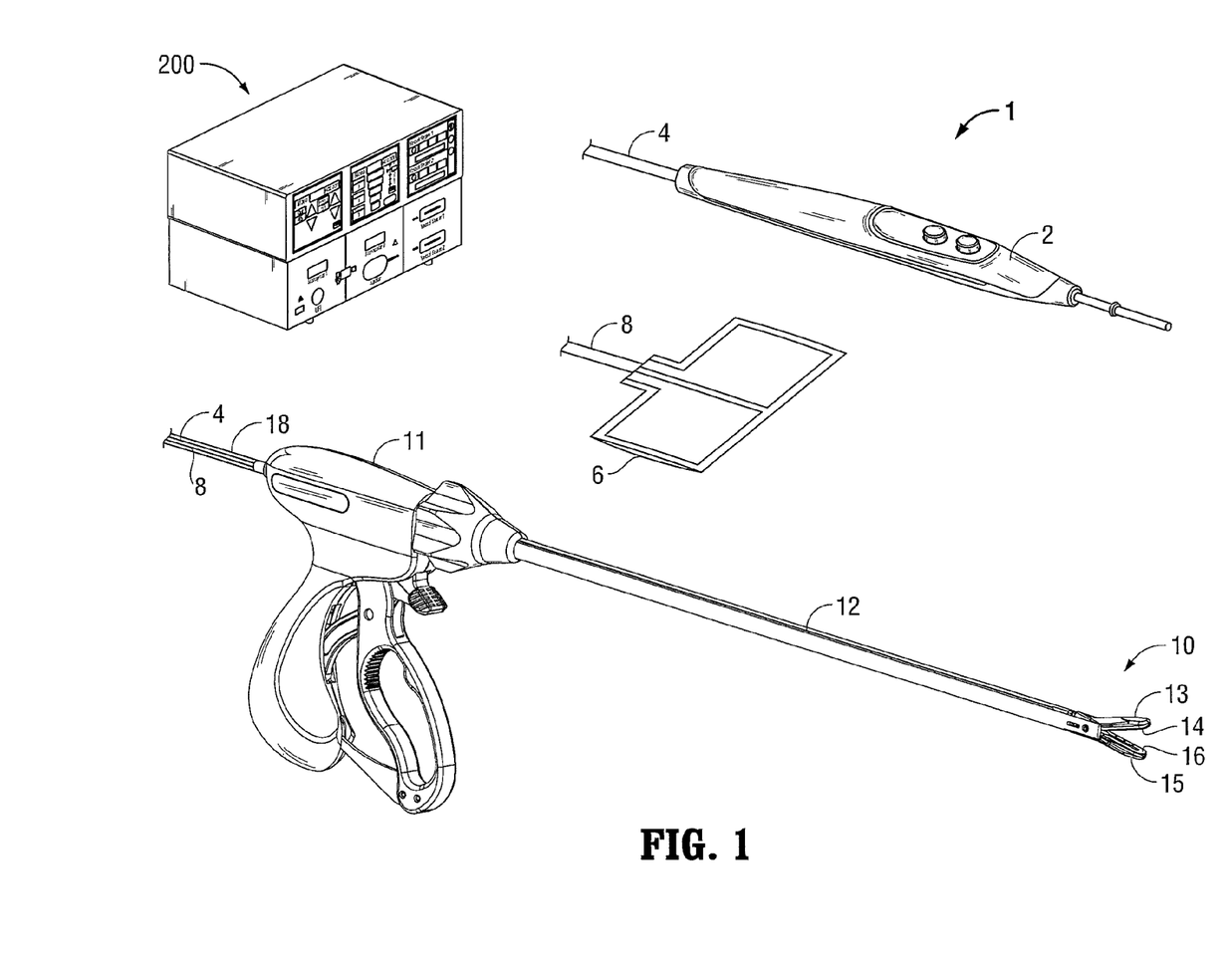
FIG. 1 is a schematic block diagram of an embodiment of an electrosurgical system according to the present disclosure.

FIG. 1 is a schematic illustration of a bipolar and monopolar electrosurgical system 1 according to the present disclosure. The system 1 may include one or more monopolar electrosurgical instruments 2 having one or more electrodes (e.g., electrosurgical cutting probe, ablation electrode(s), etc.) for treating tissue of a patient. Electrosurgical energy is supplied to the instrument 2 by a generator 200 via a supply line 4 that is connected to an active terminal 230 (FIG. 3) of the generator 200, allowing the instrument 2 to coagulate, ablate and/or otherwise treat tissue. The energy is returned to the generator 200 through a return electrode 6 via a return line 8 at a return terminal 32 (FIG. 3) of the generator 200. The system 1 may include a plurality of return electrodes 6 that are disposed on a patient to minimize the chances of tissue damage by maximizing the overall contact area with the patient. In addition, the generator 200 and the return electrode 6 may be configured for monitoring so-called "tissue-to-patient" contact to insure that sufficient contact exists therebetween to further minimize chances of tissue damage.

Figure 3:
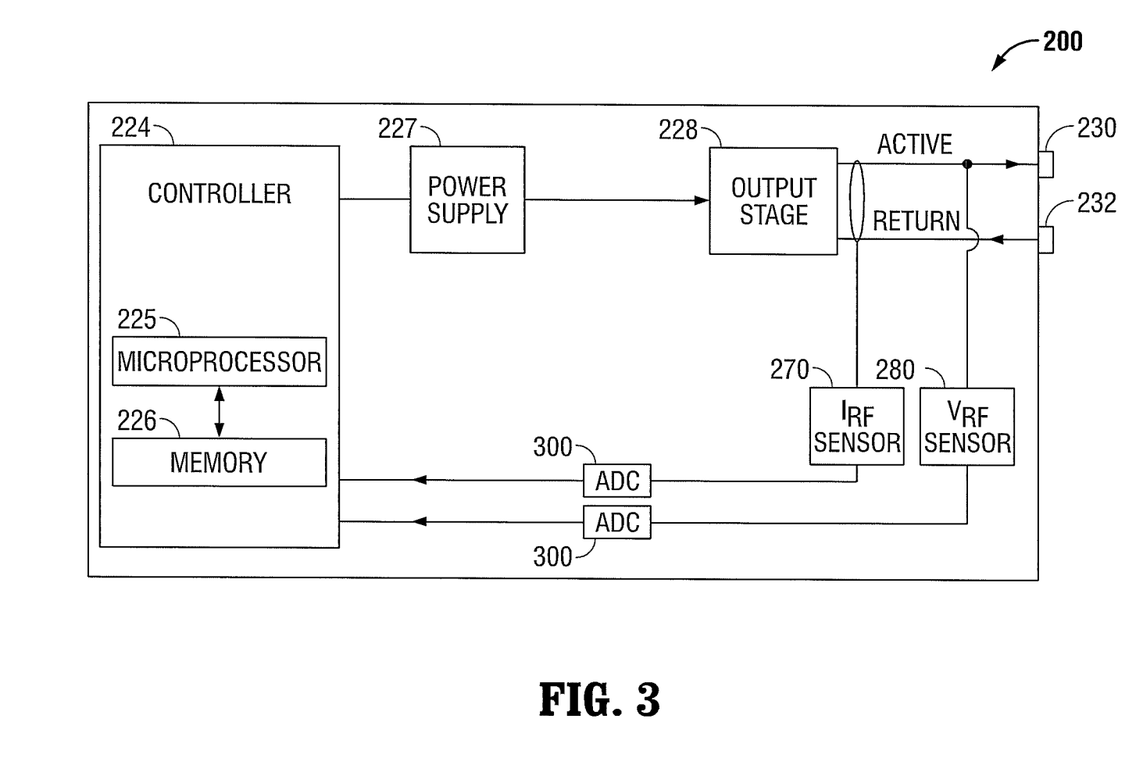
FIG. 3 is a schematic block diagram of the electrosurgical generator of FIG. 2 according to the present disclosure.

The system 1 may also include a bipolar electrosurgical forceps 10 having one or more electrodes for treating tissue of a patient. The electrosurgical forceps 10 includes a housing 11 and opposing jaw members 13 and 15 disposed at a distal end of a shaft 12. The jaw members 13 and 15 have one or more active electrodes 14 and a return electrode 16 disposed therein, respectively. The active electrode 14 and the return electrode 16 are connected to the generator 200 through cable 18 that includes the supply and return lines 4, 8 coupled to the active and return terminals 230, 232, respectively (FIG. 3). The electrosurgical forceps 10 is coupled to the generator 200 at a connector having connections to the active and return terminals 230 and 232 (e.g., pins) via a plug disposed at the end of the cable 18, wherein the plug includes contacts from the supply and return lines 4, 8 as discussed in more detail below.

Figure 2:
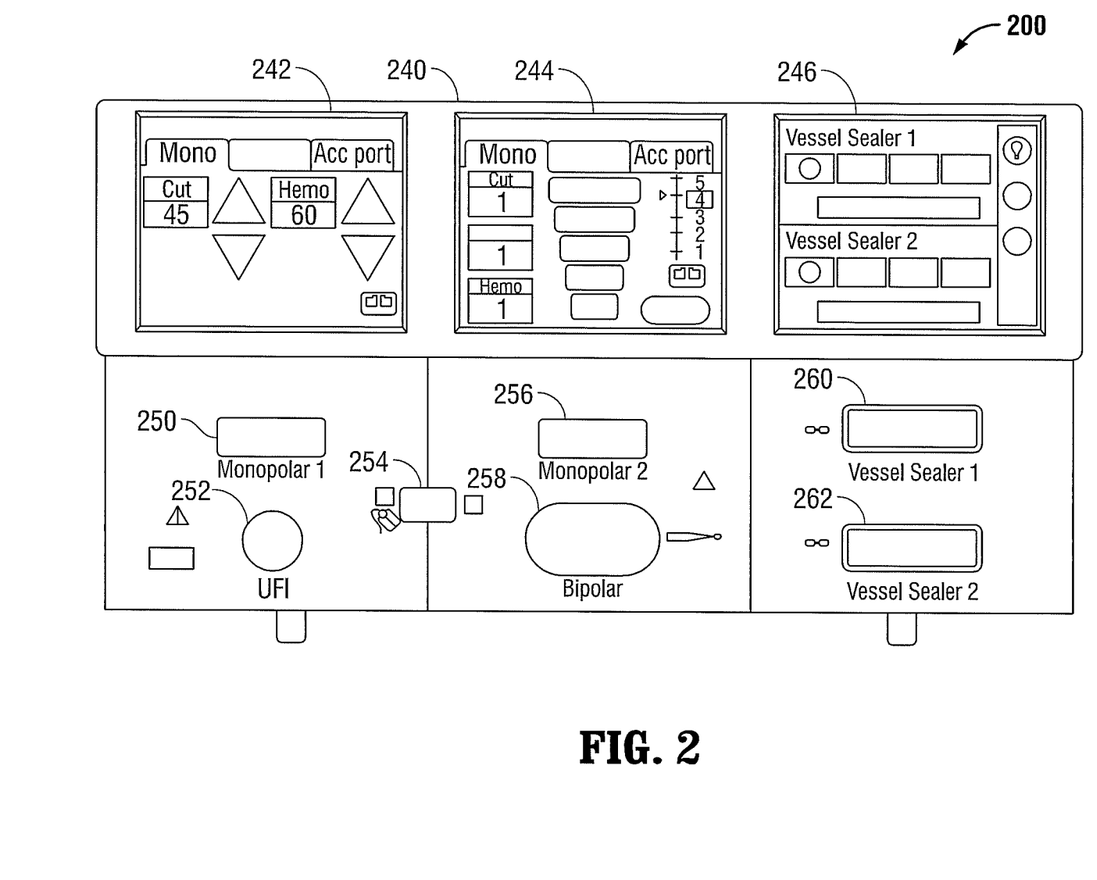
FIG. 2 is a front view of an electrosurgical generator according to the present disclosure.

With reference to FIG. 2, a front face 240 of the generator 200 is shown. The generator 200 may be any suitable type (e.g., electrosurgical, microwave, etc.) and may include a plurality of connectors 250-262 to accommodate various types of electrosurgical instruments (e.g., electrosurgical forceps 10, etc.). The connectors 250-262 may include various detection devices that can read (e.g., scan, decode, etc.) identifying information encoded or otherwise recorded on or within the plugs or cables of the instruments. The connectors 250-262 are configured to decode the information encoded on the plugs corresponding to the operating parameters of particular instruments allowing the generator 200 to preset energy delivery settings based on the connected instrument. In embodiments, data may be encoded in bar codes, electrical components (e.g., resistors, capacitors, etc.), RFID chips, magnets, non-transitory storage (e.g., non-volatile memory, EEPROM, etc.), which may then be coupled to or integrated into the plug. Corresponding detection devices may include, but are not limited to, bar code readers, electrical sensors, RFID readers, Hall Effect sensors, memory readers, etc. and any other suitable decoders configured to decode data.

The generator 200 includes one or more display screens 242, 244, 246 for providing the user with variety of output information (e.g., intensity settings, treatment complete indicators, etc.). Each of the screens 242, 244, 246 is associated with corresponding connector 250-262. The generator 200 includes suitable input controls (e.g., buttons, activators, switches, touch screen, etc.) for controlling the generator 200. The display screens 242, 244, 246 are also configured as touch screens that display a corresponding menu for the electrosurgical instruments (e.g., electrosurgical forceps 10, etc.). The user then makes inputs by simply touching corresponding menu options.

Screen 242 controls monopolar output and the devices connected to the connectors 250 and 252. Connector 250 is configured to couple to monopolar electrosurgical instrument (e.g., electrosurgical pencil) and connector 252 is configured to couple to a foot switch (not shown). The foot switch provides for additional inputs (e.g., replicating inputs of the generator 200). Screen 244 controls monopolar and bipolar output and the devices connected to the connectors 256 and 258. Connector 256 is configured to couple to other monopolar instruments. Connector 258 is configured to couple to a bipolar instrument (not shown).

Screen 246 controls bipolar sealing procedures performed by the forceps 10 that may be plugged into the connectors 260 and 262. The generator 200 outputs energy through the connectors 260 and 262 suitable for sealing tissue grasped by the forceps 10. In particular, screen 246 outputs a user interface that allows the user to input a user-defined intensity setting. The user-defined setting may be any setting that allows the user to adjust one or more energy delivery parameters, such as power, current, voltage, energy, etc. or sealing parameters, such as pressure, sealing duration, etc. The user-defined setting is transmitted to the controller 224 where the setting may be saved in memory 226. In embodiments, the intensity setting may be a number scale, such as from one to ten or one to five. In embodiments, the intensity setting may be associated with an output curve of the generator 200. The intensity settings may be specific for each forceps 10 being utilized, such that various instruments provide the user with a specific intensity scale corresponding to the forceps 10.

FIG. 3 shows a schematic block diagram of the generator 200 configured to output electrosurgical energy. The generator 200 includes a controller 224, a power supply 227, and an output stage 228. The power supply 227 may be a direct current high voltage power supply and is connected to an AC source (e.g., line voltage) and provides high voltage DC power to an output stage 228, which then converts high voltage DC power into treatment energy (e.g., ultrasonic, electrosurgical or microwave) and delivers the energy to the active terminal 230. The energy is returned thereto via the return terminal 232. The output stage 228 is configured to operate in a plurality of modes, during which the generator 200 outputs corresponding waveforms having specific duty cycles, peak voltages, crest factors, etc. In another embodiment, the generator 200 may be based on other types of suitable power supply topologies.

The controller 224 includes a microprocessor 225 operably connected to a memory 226, which may include transitory type memory (e.g., RAM) and/or non-transitory type memory (e.g., flash media, disk media, etc.). The microprocessor 225 includes an output port that is operably connected to the power supply 227 and/or output stage 228 allowing the microprocessor 225 to control the output of the generator 200 according to either open and/or closed control loop schemes. Those skilled in the art will appreciate that the microprocessor 225 may be substituted by any logic processor (e.g., control circuit) adapted to perform the calculations and/or set of instructions discussed herein.

A closed loop control scheme is a feedback control loop, in which one or more sensors measure a variety of tissue and energy properties (e.g., tissue impedance, tissue temperature, output power, current and/or voltage, etc.), and provide feedback to the controller 224. The controller 224 then signals the power supply 227 and/or output stage 228, which then adjusts the DC and/or power supply, respectively. The controller 224 also receives input signals from the input controls of the generator 200, the instrument 2 and/or forceps 10. The controller 224 utilizes the input signals to adjust power outputted by the generator 200 and/or performs other control functions thereon.

The generator 200 according to the present disclosure includes an RF current sensor 270 and an RF voltage sensor 280. The RF current sensor 270 is coupled to the active terminal 230 and provides measurements of the RF current supplied by the output stage 228. The RF voltage sensor 280 is coupled to the active and return terminals 230 and 232 and provides measurements of the RF voltage supplied by the output stage 228. In embodiments, the RF current and voltage sensors 270 and 280 may be coupled to active and return leads 228a and 228b, which interconnect the active and return terminals 230 and 232 to the output stage 228, respectively. The RF current and voltage sensors 270 and 280 provide the sensed RF voltage and current signals, respectively, to the controller 224, which then may adjust output of the power supply 227 and/or the output stage 228 in response to the sensed RF voltage and current signals. Various components of the generator 200, namely, the output stage 228, the RF current and voltage sensors 270 and 280, may be disposed on a printed circuit board (PCB).

The controller 224 may include or be coupled to one or more analog-to-digital converters (ADC) 300 that are configured to convert analog signals from the sensors 270 and 280 or other analog components of the generator 200 into digital sensor signals suitable for processing by the processor 225. The ADC 300 may be any suitable ADC having any number of bits, in embodiments from about 2 to about 16. The present disclosure provides a circuit for detecting the failure in ADC. A faulty ADC results in a loss of conversion linearity, scale, monotonicity, and combination thereof. These types of errors may be caused by a faulty reference voltage signal and/or stuck or shorted bit(s).

Figure 4:
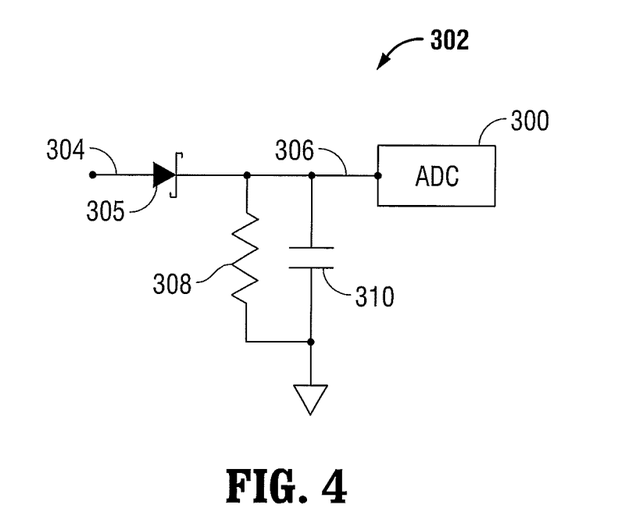
FIG. 4 is a schematic circuit diagram of a test circuit according to an embodiment of the present disclosure.

FIG. 4 shows an embodiment of a test circuit 302 according to the present disclosure. The circuit 302 includes an input 304 and an output 306. The circuit 302 further includes a diode 305 coupled to the input 304 and a resistor 308 coupled in parallel with a capacitor 310, which are grounded. The resistor 308 and the capacitor 310 are coupled between the diode 305 and the output 306.

Figure 5:
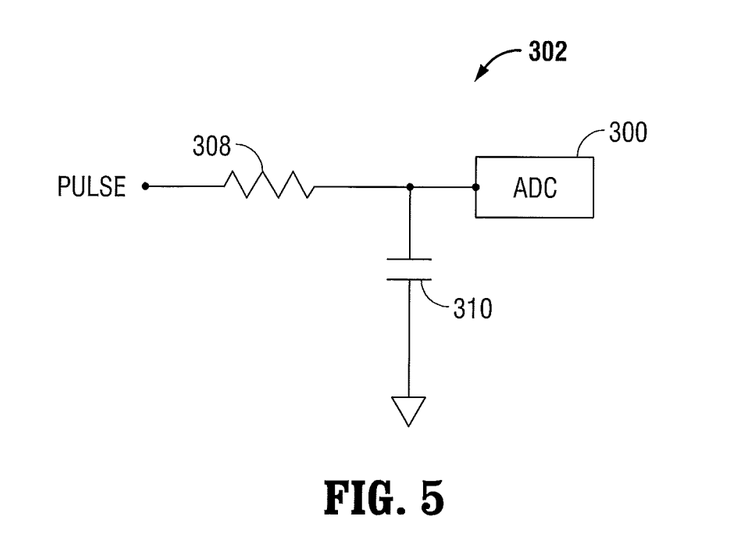
FIG. 5 is a schematic circuit diagram of a test circuit according to an embodiment of the present disclosure.

FIG. 5 shows another embodiment of the test circuit 302, with the resistor 308 being coupled in series with the capacitor 310. In this embodiment, the resistor 308 replaces the diode 305 with a slight loss of accuracy as compared with the test circuit of FIG. 4.

A test pulse, which may be a positive voltage pulse, is applied at the input 304 that charges the capacitor 310 to a predetermined voltage. The pulse may be provided by any suitable power source, e.g., the output stage 228. The test pulse may be a computer-generated signal, e.g., a square wave pulse. To allow for calibration of the response of the ADC 300, the test pulse is different form the signals under test to avoid ambiguity in the results. That is, it is provided from an orthogonal signal source that is independent from sources of possible ADC errors. In embodiments, the test pulse may be supplied to the ADC 300 via a different input pin (not shown) than the regular input (e.g., output 306) so as not to interfere with sensor accuracy. Further, the test pulse may be generated by the output stage 228 from an output port that is different from the ports powering the sensors 270 and 280.

The capacitor 310 may be charged by the pulse to a voltage that is higher than then the scale reference of the ADC 300. In embodiments, the ADC 300 may have a scale reference from about 2 V to about 3 V and the capacitor 310 may be charged to about 3.3 V. In embodiments, the pulse signal may be provided by a tri-state digital output, thereby obviating the need for the diode 305. In other words, a tri-state digital output emulates the response of the diode 305.

With reference to FIG. 4, the diode 305 charges the capacitor 310 to a known predetermined voltage via the test pulse when the source voltage is high and disconnects the source (e.g., terminate the test pulse) when the source voltage is low, so that the capacitor 310 can discharge according to a predetermined exponential decay rate.

With reference to FIG. 5, the embodiment of the test circuit 302 without the diode 305, the source voltage and the resistor 308 together perform a substantially the same function as the source voltage and diode 305, which is charge the capacitor 310 to the predetermined voltage via when the source voltage is high and disconnect the source when the source voltage is low. The source voltage test pulse may be of different durations for each embodiment to accommodate specific circuit designs.

During operation, the voltage pulse is removed, e.g., terminated and the voltage at the capacitor 310 begins to discharge asymptotically to zero at a rate determined by the values of the capacitor 310 and resistor 308. Since the discharge curve is very predictable and repeatable the value of the voltage supplied to the ADC 300 can be very precisely calculated.

The output of the ADC 300 may be supplied to the processor 225, which then compares the output of the ADC 300 to a preprogrammed response that may be stored in the memory 226. By taking successive samples from the ADC 300 at the output 306 of the resulting voltage decay at precise times or intervals, and/or sampling repeated decay cycles, linearity, slope and monotonicity may be uniquely determined. Thus an error in linearity, slope or monotonicity in the ADC conversions may be used to determine and characterize the magnitude and severity of a fault in the operation of the ADC 300 and appropriate action may be taken to minimize the effects of the errors on system performance.

Figure 6:
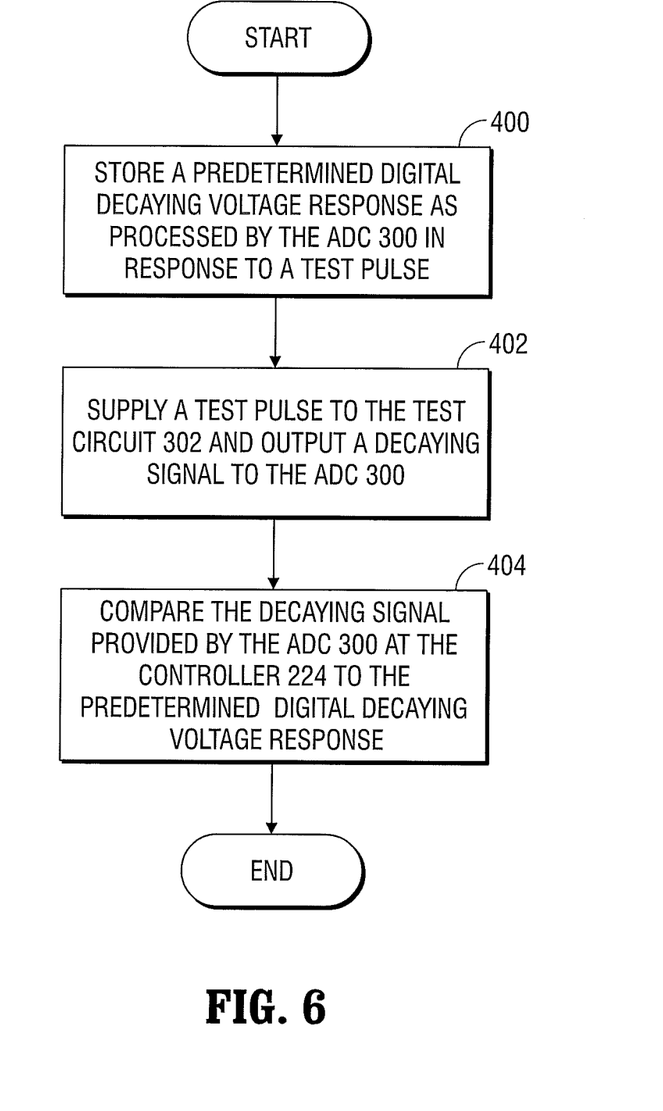
FIG. 6 is a flow chart of a method according to the present disclosure.

FIG. 6 shows a method for testing operation of the ADC 300 according to the present disclosure. In step 400, the controller 224 stores a predetermined digital decaying voltage response as processed by the ADC 300 in response to a test pulse. The decay response may be stored in memory 226. During testing, in step 402, a test pulse is supplied to the test circuit 302, which provides a decaying signal to the ADC 300. In step 404, the controller 224 compares the decaying signal provided by the ADC 300 to the saved signal response stored in the memory 226. Any significant deviation between the responses, e.g., 10% or more, would be indicative of the malfunctioning ADC 300. The method may be performed at any time during the operation of the generator 200.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for testing an analog-to-digital converter, comprising:
    a test pulse source configured to provide a test pulse signal;
    a test circuit coupled to the test pulse source and configured to provide an analog decaying voltage signal in response to the test pulse signal;
    an analog-to-digital converter coupled to the test circuit and configured to convert the analog decaying voltage signal into a digital decaying voltage signal; and
    a controller coupled to the analog-to-digital converter, the controller including a memory storing a predetermined digital decaying voltage response of the analog-to-digital converter, wherein the controller is configured to compare the digital decaying voltage signal to the predetermined digital decaying voltage response.

2. The system according to claim 1, wherein the controller is configured to output an error signal in response to a deviation between the digital decaying voltage signal and the predetermined digital decaying voltage response.

3. The system according to claim 1, wherein the test circuit comprises:
    an input coupled to the test pulse source;
    a resistor coupled to the input;
    a capacitor coupled to the resistor; and
    an output coupled to the capacitor and the analog-to-digital converter.

4. The system according to claim 3, wherein the resistor is coupled in series with the capacitor.

5. The system according to claim 3, wherein the test circuit further comprises:
    a diode coupled to the input and the resistor.

6. The system according to claim 5, wherein the resistor is coupled in parallel with the capacitor.

7. The system according to claim 1, wherein the test pulse source is configured to provide a tri-state digital output.

8. An electrosurgical system, comprising:
    a radio frequency output stage configured to generate radio frequency energy;
    a sensor coupled to the radio frequency output stage configured to sense at least one property of the radio frequency energy;
    a test pulse source configured to provide a test pulse signal;
    a test circuit coupled to the test pulse source and configured to provide an analog decaying voltage signal in response to the test pulse signal;
    an analog-to-digital converter coupled to the test circuit and configured to convert the analog decaying voltage signal into a digital decaying voltage signal; and
    a controller coupled to the analog-to-digital converter, the controller including a memory storing a predetermined digital decaying voltage response of the analog-to-digital converter, wherein the controller is configured to compare the digital decaying voltage signal to the predetermined digital decaying voltage response.

9. The system according to claim 8, wherein the controller is configured to output an error signal in response to a deviation between the digital decaying voltage signal and the predetermined digital decaying voltage response.

10. The system according to claim 8, wherein the test circuit comprises:
an input coupled to the test pulse source;
a resistor coupled to the input;
a capacitor coupled to the resistor; and
an output coupled to the capacitor and the analog-to-digital converter.

11. The system according to claim 10, wherein the resistor is coupled in series with the capacitor.

12. The system according to claim 10, wherein the test circuit further comprises:
a diode coupled to the input and the resistor.

13. The system according to claim 12, wherein the resistor is coupled in parallel with the capacitor.

14. A method for testing an analog-to-digital converter, comprising:
providing a test pulse signal to a test circuit coupled to the analog-to-digital converter;
generating an analog decaying voltage signal in response to the test pulse signal;
converting the analog decaying voltage signal into a digital decaying voltage signal;
storing a predetermined digital decaying voltage response of the analog-to-digital converter in a memory; and
comparing the digital decaying voltage signal to the predetermined digital decaying voltage response.

15. The method according to claim 14, further comprising:
outputting an error signal in response to a deviation between the digital decaying voltage signal and the predetermined digital decaying voltage response.

16. The method according to claim 14, wherein the test circuit comprises:
an input coupled to the test pulse source;
a resistor coupled to the input;
a capacitor coupled to the resistor; and
an output coupled to the capacitor and the analog-to-digital converter.

\* \* \* \* \*